United States Patent [19]

Dillon et al.

[11] Patent Number: 4,915,847
[45] Date of Patent: Apr. 10, 1990

[54] CRYOGLOBULIN SEPARATION

[75] Inventors: David M. Dillon, Dover; Stephen H. Franks, Hopkinton, both of Mass.

[73] Assignee: Baxter International Inc., Deerfield, Ill.

[21] Appl. No.: 81,484

[22] Filed: Aug. 4, 1987

[51] Int. Cl.$^4$ .............................................. B01D 21/26
[52] U.S. Cl. ................................... 210/737; 210/321.6; 210/472; 210/515; 210/539; 210/782; 210/789; 422/101; 422/102; 494/37; 604/410; 424/101; 530/380; 530/383; 530/830
[58] Field of Search ............... 604/4, 6, 406, 408, 604/410; 494/16, 18, 17, 37; 422/101, 102; 210/737, 782, 787, 789, 321.6, 360.1, 361, 369, 380.1, 472, 514, 515, 539, 774; 530/380, 383, 830; 424/101

[56] References Cited

U.S. PATENT DOCUMENTS

| | | | |
|---|---|---|---|
| 3,481,712 | 12/1969 | Bernstein | 422/102 |
| 3,545,671 | 12/1970 | Ross | |
| 3,750,645 | 8/1973 | Bennett et al. | 210/361 |
| 3,870,042 | 3/1975 | Viguier | |
| 3,897,902 | 8/1975 | Yanez, Jr. | 210/789 X |
| 3,986,506 | 10/1976 | Garber et al. | 604/406 |
| 4,040,959 | 8/1977 | Berman et al. | 210/515 |
| 4,141,887 | 2/1979 | Seufert | |
| 4,310,488 | 1/1982 | Rahm et al. | 422/102 |
| 4,335,730 | 6/1982 | Griffen | 422/102 X |
| 4,364,903 | 12/1982 | Bittings | 422/101 |
| 4,483,825 | 11/1984 | Fatches | 422/101 X |
| 4,537,308 | 8/1985 | Hollander, Jr. | 206/484 |
| 4,588,554 | 5/1986 | Kaartinen et al. | 604/410 |
| 4,617,009 | 10/1986 | Ohlin et al. | 494/21 |
| 4,698,311 | 10/1987 | Hall et al. | 210/789 |
| 4,720,284 | 1/1988 | McCarty | 494/37 |

OTHER PUBLICATIONS

"Now the way is clear . . . with the Cutter Leukotrap Platelet Pooling System" Miles Laboratories (1985) CB-676.

Primary Examiner—W. Gary Jones
Attorney, Agent, or Firm—Paul C. Flattery; Bradford R. L. Price; Robert M. Barrett

[57] ABSTRACT

A set for the isolation of cryoprecipitate includes a hollow vessel with first and second ends and a tapered body extending to a narrow sump closing the second end, said sump enclosing a volume of approximately 2 to 5 percent of the volume of the hollow vessel. A port enters the vessel in the tapered body above the sump. In one embodiment, the vessel is formed of a rigid or semi-rigid material and the first end is closed by a cap containing a micro-porous filter for venting the vessel. In another or further embodiment, the sump has a tapered tip portion which may be sliced off to permit extrusion of the isolated cryoprecipitate by squeezing the vessel. In a different embodiment, the vessel contains an inner filter column, or bag with a filter matrix, accessible via an access port. Cellular material placed in the column is frozen, thawed and centrifuged to separate out antigen-free platelet growth factor with the cryoprecipitate.

8 Claims, 6 Drawing Sheets

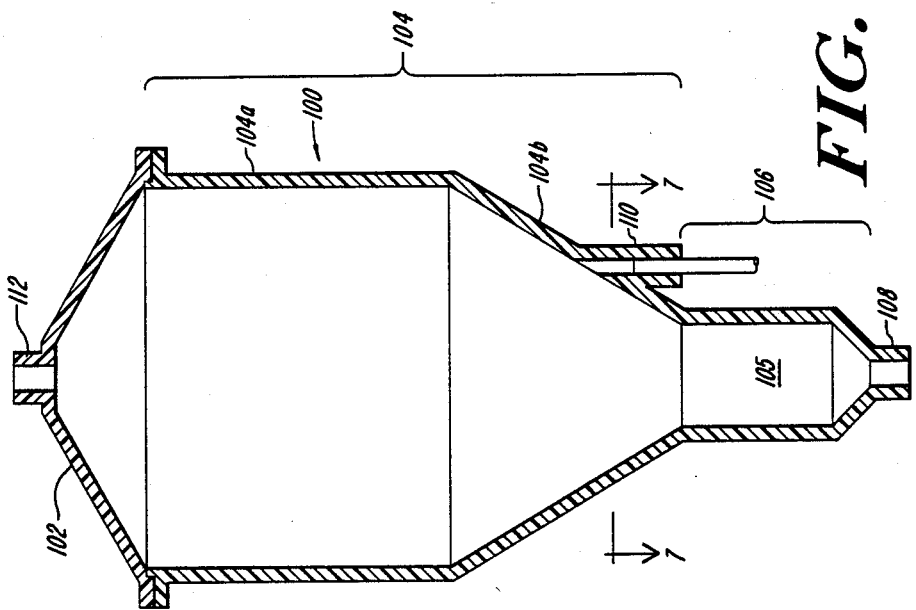
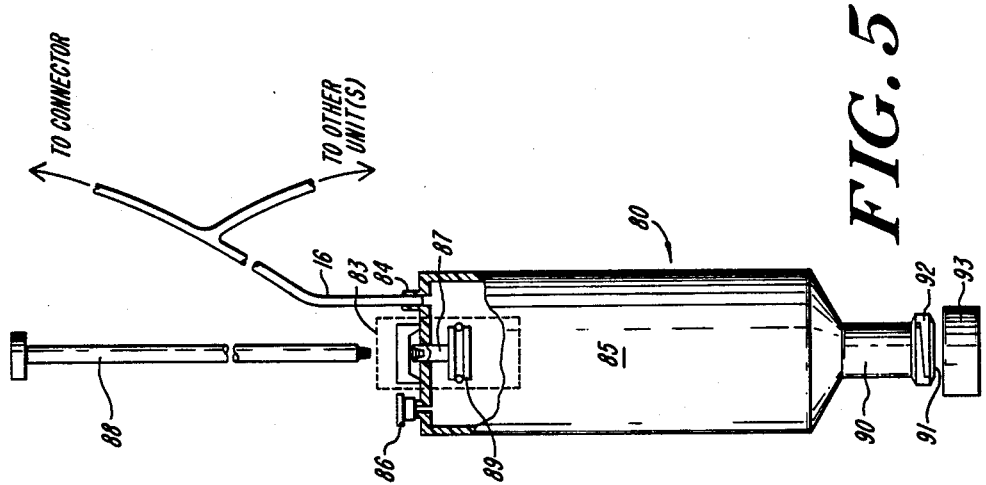

CRYOGLOBULIN SEPARATION

BACKGROUND OF THE INVENTION

This invention relates to blood separation methods and apparatus, and more particularly to the isolation of cryoprecipitate or cryoglobulin.

Cryoprecipitate, isolated from blood plasma, is rich in clotting factors. For this reason, it has long been used for the treatment of hemophilia. More recently, it has been proposed to make a "fibrin glue" for sealing surgical joins using a multi-part mixture of cryoprecipitate, thrombin and calcium chloride. Cryoprecipitate alone has also been reported as suitable for such use, especially as a natural clotting sealant around sutured joins of arterial or venous tissue. Although of lesser tensile strength than a fibrin glue composition, approximately 2 to 3 percent of plasma may be isolated as cryoprecipitate, and the isolation may be performed in a hospital blood bank. Thus, autologous aliquots of "cryo" for surgical use may be prepared. This offers great promise in heart surgery, where suture bleeding, and patient cross reactions to blood-derived agents are both particularly grave problems.

The standard procedure for isolating cryoprecipitate uses a conventional phlebotomy set. The blood is drawn and anticoagulated, and centrifuged to separate the plasma. The plasma is expressed to the plasma bag, which is then sealed. The plasma bag is then frozen and thawed, which results in the precipitation of cryoprecipitate as a whitish factor. The cryoprecipitate is then separated from the plasma by centrifuging the plasma bag, and expressing the lighter cryo-poor fraction from the bag, leaving the cryoprecipitate fraction of 4–8 milliliters in the bag. Alternatively, the thawed plasma may be centrifuged in one or more centrifuge tubes, isolating the cryoprecipitate as a highly viscous plug in the bottom of each tube.

The separated material may be used by daubing about a surgical site with a spatula, or may be refrozen and thawed to result in a thinner, injectable form of cryoprecipitate such as used for the aforementioned treatment of hemophilia.

OBJECTS AND SUMMARY OF THE INVENTION

It is an object of the invention to provide an improved method and vessel for the isolation of cryoprecipitate.

It is another object of the invention to Provide a vessel for the isolation of cryoprecipitate which is adapted for aseptic or sterile docking and storage.

It is another object of the invention to provide a vessel for the isolation of cryoprecipitate which is also an applicator for the topical application of the cryoprecipitate to a surgical site.

These and other desirable features are obtained in a set for the isolation of cryoprecipitate having a hollow cylindrical vessel with a first closed end, a second end and a longitudinal axis, the first end having a port with a sterile docking connector for transferring plasma between the vessel and a plasma bag, and the second end having a nipple extending from and closing the second end. Preferably the nipple has a generally cylindrical shape and encloses a volume of approximately 2 to 5 percent of the volume of the vessel.

In one embodiment, the vessel is formed of a semi-rigid material and the first end is closed by a cap containing a micro-porous filter for venting the vessel during transfer of plasma through the port. In another or further embodiment, the nipple has a tip portion which may be sliced off to permit extrusion of the isolated cryoprecipitate by squeezing the vessel. In a different further embodiment, the nipple has a twist-lockable connector, such as a Luer fitting, for attachment to a syringe or to an applicator tip. A presently preferred embodiment includes plural vessels, each with an end cap and a nipple, wherein all the end caps are connected to a common sterile docking connector. The total volume of the plural vessels is approximately 250 to 350 milliliters, for holding the plasma from one unit of whole blood.

A method for the isolation of cryoprecipitate according to the invention includes the steps of separating plasma from whole blood, transferring the plasma to the one or more vessels according to the invention, freezing and thawing the plasma, and centrifuging the vessels to isolate the cryoprecipitate in the nipple end of each vessel. After isolation according to the invention, the cryo-poor plasma is decanted from each vessel through its port, and the vessels, each with a plug of cryoprecipitate in its nipple end, are stored as sterile aliquots for surgical or medical use. In a further method according to the invention, the cryoprecipitate is applied directly to a surgical site by extruding it from the nipple.

BRIEF DESCRIPTION OF THE DRAWINGS

FIG. 5 shows another embodiment of the invention with an integral extrusion mechanism;

FIG. 6 shows a longitudinal cross-section of another embodiment of a cryoglobulin separation vessel;

DETAILED DESCRIPTION OF ILLUSTRATED EMBODIMENTS

Figure 1:
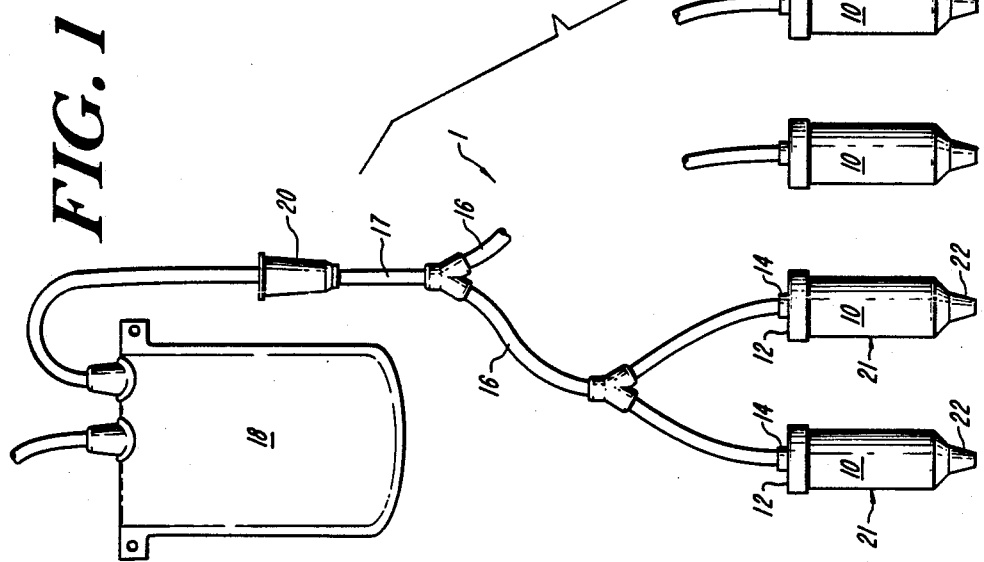
FIG. 1 is a schematic illustration of the invention with a plasma bag of a phlebotomy set.

FIG. 1 shows a schematic illustration of a set 1 according to a basic embodiment of the invention. Set 1 includes a plurality of vessels 10 each having an inlet end 12 with a port 14. A branch tube 16 runs from each port 14 to a common tube 17 which connects to a plasma bag 18. The plasma bag 18 may be the plasma receiving bag of a conventional phlebotomy set, and tube 17 may connect in a conventional manner to such bag so as to form a sterile system. Alternatively, the entire set including bag 18 tubes 17, 16 and vessels 10 may be formed as a sterile sealed unit. Preferably, tube 17 connects to plasma bag 18 via a spike or other fitting 20, which is preferably a sterile docking fitting.

Each vessel 10 has a generally cylindrical body 20 which extends from an inlet cap 12 which closes one end to a collection end 22 with the shape of a small substantially cylindrical nipple which closes the other end of the cylinder. The nipple structure is located to receive the densest faction of plasma during centrifuging, and is dimensioned to accommodate the amount of cryoprecipitate yielded by the volume of plasma held by the vessel 10.

Figure 2A:
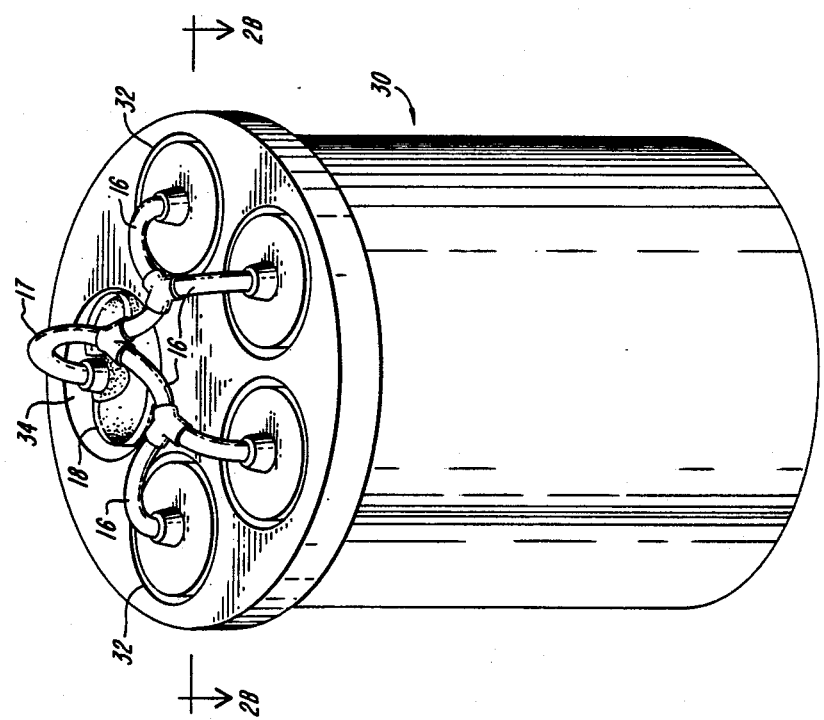
FIGS. 2A, 2B show a plan view from above, and a vertical section, respectively, of the set of FIG. 1 in a support fixture for centrifuging.
Figure 2B:
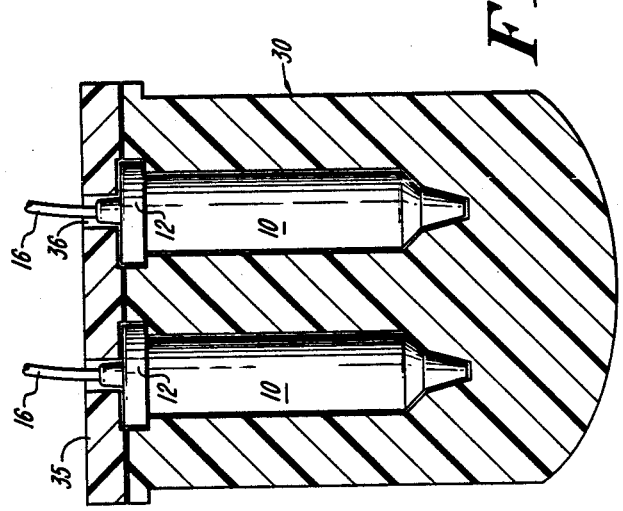

FIGS. 2A, 2B show a top perspective view and a section, respectively of a four vessel set according to FIG. 1 held in a support fixture for centrifuging. Vessels 10 are each inserted in a cylindrical well 32 of the fixture 30, and tubes 16, 17 connect the vessels to the plasma bag 18. As discussed in connection with the method for practicing the invention, below, the contents of bag 18 have been expressed into the vessels 10 and bag 18, which is empty, is rolled up and inserted in another recess 34 of fixture 30. FIG. 2B is a vertical section along the planes indicated in FIG. 2A, through the fixture 30 and passing through two of the recesses 32. As shown, the cylindrical wells 32 of the fixture 30 have solid walls defining a contour identical to that of the vessels 10 so that each vessel is rigidly supported about its entire outside surface. A cover plate 35 having slots for the Passage of tubes 16, 17 therethrough may be fitted over the fixture in the centrifuge bucket so as to provide a complete pressure resisting housing around the set during centrifuging.

The method of separating cryoprecipitate according to the invention proceeds as follows. First, after blood is drawn, anticoagulated and separated, the plasma is expressed off into a plasma bag 18. The plasma is then expressed into the vessels 10 which are dimensioned to receive the entire volume of plasma from one unit of whole blood. According to standard blood bank practice in the United States, a unit of whole blood has a blood volume of about 450 milliliters, and yields 200-300 or more milliliters of plasma. Thus, for example, there may be four vessels 10 each having a volume of approximately 60 milliliters, three having a volume in the range of 80 milliliters or even a single large 250 milliliter vessel. Either before or after such transfer, the plasma is frozen and then thawed to precipitate out the cryoprecipitate. A good yield is obtained by completely freezing to minus thirty degrees C., thawing in a refrigerator at two to six degrees C. and centrifuging at two to five thousand g (RCF) for ten to thirty minutes.

Vessels 10 and the empty plasma bag 18 are then placed in the fixture 30 described above and centrifuged at a speed and for a time sufficient to separate out the cryoprecipitate as a viscous mass in the nipple 22. The centrifuge is then stopped, the vessels 10 and bag 18 removed therefrom, and the cryo-poor plasma faction is decanted from each vessel back into the plasma bag 18, whence it may be returned to the donor or otherwise used. Each vessel 10 then contains one aliquot of cryoprecipitate from its corresponding volume of plasma.

These aliquots may then be stored, processed or used immediately.

It will be appreciated that with a unitary set as shown in FIG. 1, or a tubing and vessel set adapted for sterile docking, the units of cryoprecipitate thus isolated will be sterile and may be banked for surgical use. In particular, since the separation is accomplished using a normal blood bank centrifuge with the set 1 and fixture 30, cryoprecipitate may be prepared from a patient's own blood in preparation for a surgical procedure on the Patient weeks in advance, substantially lessening the risks of infection or rejection reactions inherent in the use of pooled blood products or in the use of blood products from other donors.

Figure 3:
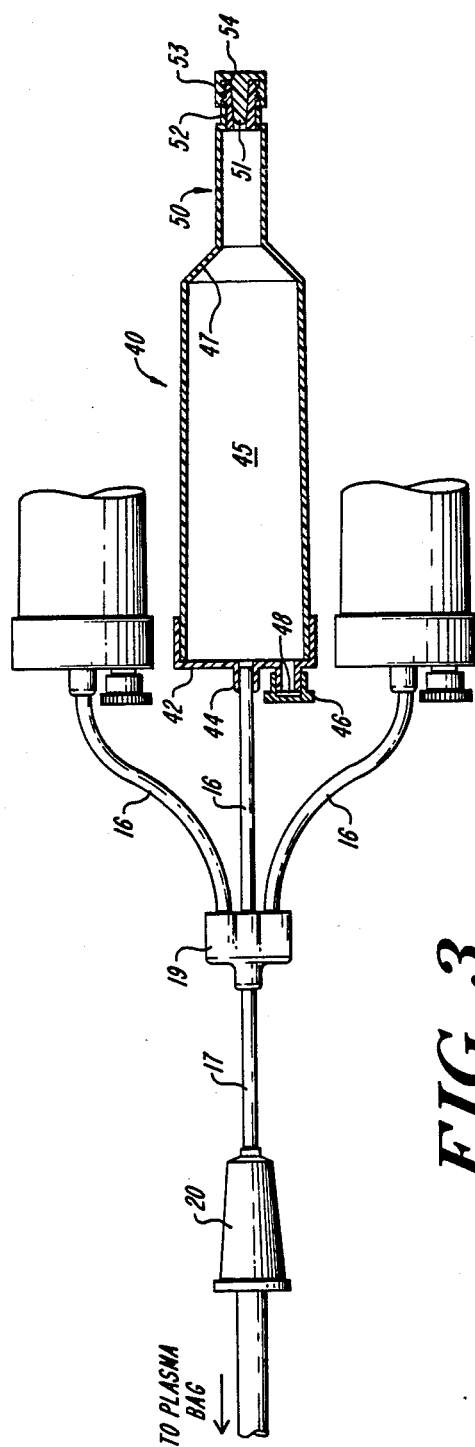
FIG. 3 shows a schematic section of a preferred embodiment of a three-vessel sterile docking set.

FIG. 3 shows a partial view and section of a preferred embodiment of a three vessel sterile docking set for the isolation of cryoprecipitate according to the invention. In this embodiment, a capped bag spike 20 connects to tube 17 which communicates via a trifurcated adaptor manifold 19 to three tubes 16, which extend to respective collection vessels 40. A suitable adaptor manifold 19 is a Medex part no. B-1450-09. Each vessel 40 has a generally cylindrical body 45 with a cap 42 at one end and a nipple portion 50 at the other end. Body 45 is preferably formed of a semi-rigid material such as a thick walled polyvinyl chloride plastic, and has an interior volume in the range of 60 to 80 milliliters. End cap 42 is formed with an inlet port 44 and also a vent 46 which permits the displacement of air when plasma is transferred from a plasma bag to the vessel or vice versa. Vent 46 includes a hydrophobic micro-porous filter 48 having a pore size in the range of 0.45 microns for preventing the influx of contaminants while permitting gas to vent therethrough. A suitable filter is a membrane-type filter sold by the Burron Medical Products company of Pennsylvania as their filter membrane, part no. A-700 4020. Cap 42 is cemented or otherwise bonded to body 45 for sealing the end thereof.

At the other end of the vessel body 45 a curved or funnel shaped wall 47 leads smoothly into the nipple end 50 which has a generally cylindrical or substantially tubular shape and is dimensioned so as to have an interior volume in the range 2 to 5 percent of the volume of the body 45. Nipple 50 extends to an outlet end which is adapted for connection to a separate device for transfer of the separated cryoprecipitate or for direct application of the separated precipitate to a surgical site. In this embodiment, nipple 50 has an interior wall 51 at its extreme tip which is tapered as a female Luer lock so that a syringe may be directly attached to the tip to draw out the separated precipitate and to allow a surgeon to use a syringe as an applicator of the precipitate to a surgical site. Nipple 50 has an external wall 52 which is threaded as a male twist-lock connection, i.e., a male Luer fitting. Nipple 50 is thus also adapted for directly connecting to a twist lockable cannula or needle for directly extruding the cryoprecipitate onto a surgical site. A Luer lock cap 53, such as the Luer cap part no. B-1500-30 sold by the Medex company of Ohio having a twist-lock inner surface 54 closes the end of the nipple so that the entire set comprising vessel(s) 40 with spike and supply tubes 16, 17 constitutes a sterile closed system.

Figure 4:
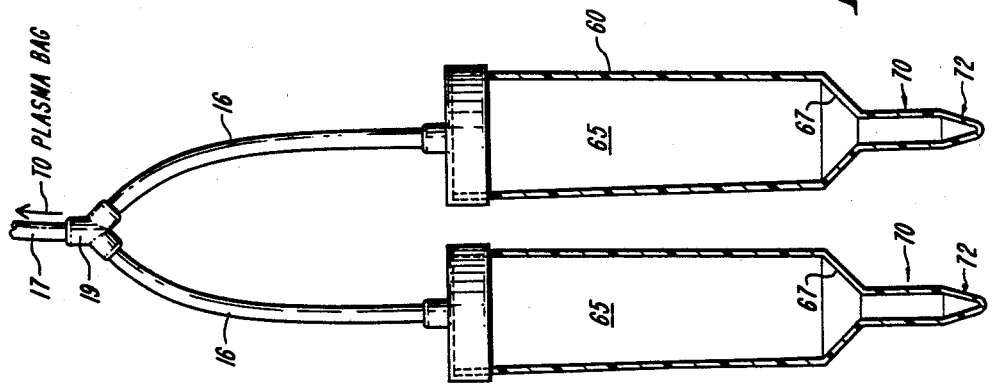
FIG. 4 shows a section of another embodiment of the invention.

FIG. 4 shows another embodiment of the invention having vessels 60, in a similar sectional view. Two vessels are shown connected to a common manifold 19 and supply tube 17. Although two vessels are shown, one, or any number (n) may be used. In this embodiment, vessel 60 includes a cylindrical body 65 having a volume of approximately 250/n milliliters, and tapering at wall 67 to a nipple portion 70. Nipple portion 70 has a conically pointed nose 72 which may be sliced off, in the manner of caulking cartridge, so as to provide an outlet for the separated cryoprecipitate therein. Vessel 60 is formed of a semi-rigid but sufficiently flexible material, such as a 0.030 to 0.040 inch thick flexible PVC, so that with the inlet tube 16 sealed closed, the vessel 60 may be squeezed by hand to extrude the precipitate from the end 72 of the vessel. The conical end has a taper of approximately fifteen degrees, terminating in a tip having an inner spherical radius in the range of (0.05) to (0.10) inches, thus providing both a degree of operator visibility, and a fine extrusion filament of precipitate when so squeezed. No vent structure is shown, although a vent similar to the structure 46, 48 of FIG. 3, or a simple return breather tube extending from the vessel 60 to the plasma bag may be employed during the plasma filling and separating stePs. Such tube or other vent is then sealed, clamped or capped prior to using the vessel 60 as a pressurized extruding device.

FIG. 5 shows yet another embodiment of a vessel 80 according to the invention having a body 85 and a nipple portion 90. As in the device of FIG. 3, nipple 90 has an open tip with an inner surface 91 and an outer surface 92 configured for twist lockable connection to a mating Luer fitting. A cap 93 closes the end. In this embodiment, the body of vessel 80 is formed of a substantially rigid material such as a polycarbonate plastic, and has an end cap 82 which includes, in addition to a vent 86 and an inlet port 84, a hermetically mounted piston structure 83. Piston structure 83 includes a soft rubber or similar piston 86 having a shank 87 which extends through the cap 82 and is hermetically sealed by a removable lock cap 84. Piston structure 83 is centered over the cylindrical nipple 90. A separate plunger 88 is provided, and after separation of the cryoprecipitate, the supply tube 16 may be severed and sealed so that the vessel 80, containing a sterile aliquot of cryoprecipitate, may be stored and used directly as a surgical applicator. For such use, the removable lock cap 84 is unscrewed, the Plunger push rod 88 is screwed into the shank 87 of the piston, and the piston is pushed downward into the interior bore of nipple 90 to extrude the precipitate. Shank 87 may be fashioned as a break-away portion of the cap, or as a flexible stopper-like fitting which is driven through from a sealing position in a mating hole in the cap by plunger pressure.

FIG. 6 shows a cross-sectional view of another embodiment of a vessel 100 for the separation of cryoglobulin according to applicant's invention. Vessel 100 has a cap portion 102, a body portion 104, and a nose portion 106. In a preferred prototype of this embodiment, vessel 100 has a volume for accommodating the plasma from one unit of blood, or approximately 300 cc. The nose portion 106 encloses an interior volume 105 which serves as a cryoglobulin receiving sump of approximately ten cc, and the entire container is formed with substantially rigid or semi-rigid walls. The body portion 104 has a generally cylindrical wall portion 104a which defines a generally cylindrical plasma reservoir, and also has a generally conical wall portion 104b extending therefrom to the sump 105. In the illustrated embodiment, sump 105 has a diameter of approximately 0.8 inches, and the tapered wall portion 104b assures that the interface, after centrifuging, between the separated cryoprecipitate and the plasma has a relatively small area. This helps prevent remixing during post processing operations such as decanting the plasma.

Vessel 100 is equipped with three ports. A first port 108 is located at the tip of the nose portion, and is used in operation for access for the separated cryoglobulin after processing has been completed. This port may have a Luer fitting or other connector as described in relation to the previously described vessel embodiments. A second port 110 enters the vessel in the tapered wall portion 104b just above the receiving sump. A third port 112 is centrally located in the cap 102, and may serve as a vent during the filling and unfilling of the vessel. Port 112 contains a bacterial hydrophobic filter, and may be caPped during centrifuging, as required.

In operation, the embodiment of FIG. 6 permits the plasma to be decanted from the central port 110 located just above the plasma/cryoprecipitate separation line after processing. Thus, the vessel need not be inverted (as is the case for the vessels 20 of FIG. 1), so that air does not percolate through the fluid during any processing stage. As a further aid to the efficient decanting of separated plasma, vessel 100 is preferably formed with a longitudinally extending groove or trough 111 which extends between the upper edge of sump 105 and the lower inside edge of the opening to port 110. This groove or trough 111 is illustrated in cross-section in FIG. 7. It serves as a drainage channel through which, when the vessel is slightly tilted toward port 110, the separated plasma near the sump interface can flow without introducing turbulence and remixing at the separation line. This permits the plasma to be substantially completely decanted after processing, resulting in a clear separation of product.

Figure 7:
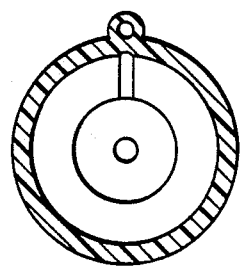
FIG. 7 shows a detail of a radial section of the vessel of FIG. 6.
Figure 8:
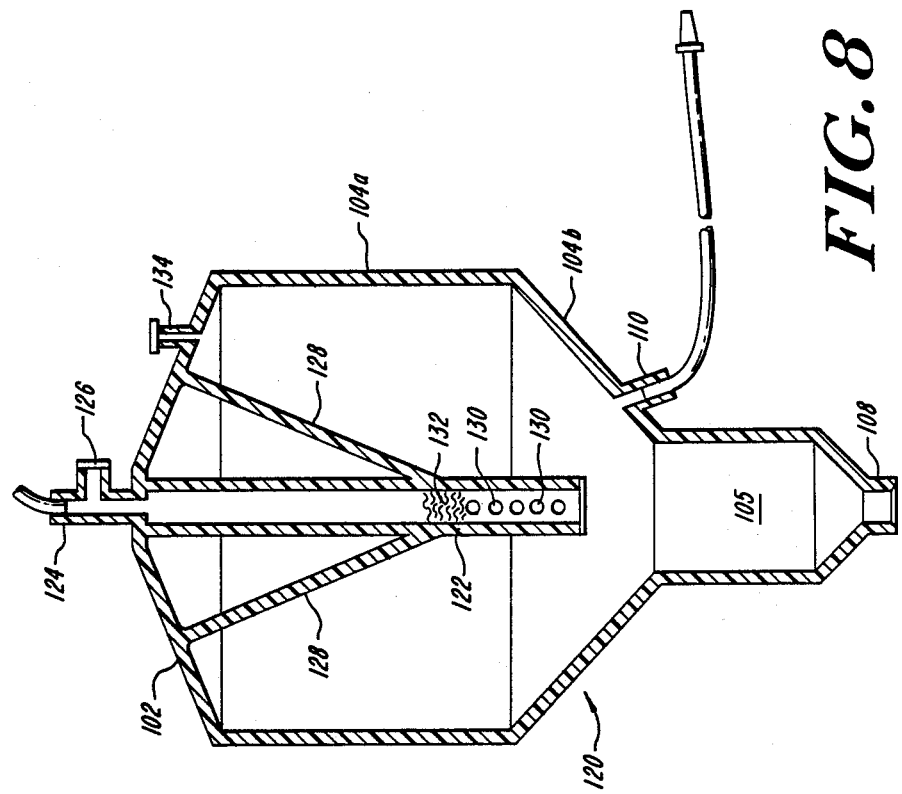
FIG. 8 shows a longitudinal cross-section of another separation vessel.

FIG. 8 shows a cross-sectional view, similar to that of FIG. 7, of yet a further embodiment of a separation vessel 120 according to the invention. Parts of vessel 120 are numbered identically to corresponding parts of vessel 100. Vessel 120 contains, in addition, a hollow interior column 122 communicating with an outlet port 124 and preferably also a vent 126, with elements 122, 124 and 126 all mounted on the cap portion 102. A plurality of ribs 128, preferably three or more, extend from the cap portion 102 to the column 122 to provide a rigid centered mounting thereon. Hollow column 122 has a plurality of apertures 130 at its lower end, and is filled with packing material 132 which provides a filtration matrix for fluids passing therethrough. Alternatively, or in addition, a microporous filter element 133 may be used. A further vent 134 is provided in the cap 102. The vessel of FIG. 8 permits the addition of biological material via port 124 into the column 122 for processing with the cryoglobulin.

One specific application of vessel 120 which applicant envisages is that platelet rich blood products may be placed in column 122 and thus may be subjected to the freezing and thawing protocols described above for the isolation of cryoprecipitate. Such freezing is expected to rupture the platelet membranes so that upon subsequent centrifuging, cellular products contained within the platelets will pass through the filtration matrix 132 into the cryoprecipitate, while the cellular membrane material will be effectively filtered out and retained within the column by the filter. Thus, vessel 120 may be used to prepare cryoprecipitate enriched with platelet growth factor, to promote enhanced recovery in topical surgical applications of cryo-glue or the cryoprecipitate as described above.

Figure 9:
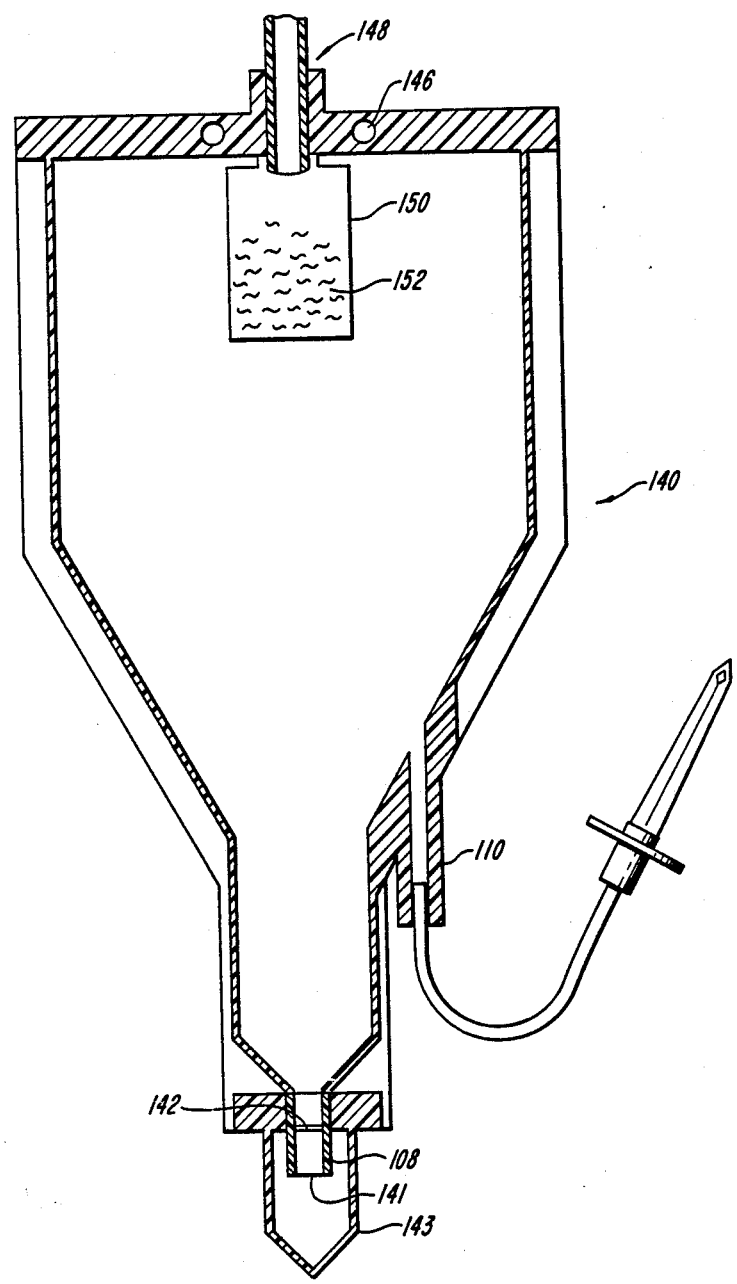
FIG. 9 shows a flexible embodiment of a separation vessel.

FIG. 9 shows a further embodiment of a separation vessel 140 which is similar in some respects to vessel 100 of FIG. 6. Vessel 140 differs in being formed as a flat bag, rather than a rigid or semi-rigid container. Vessel 140 requires no hydrophobic filters or other provision for accommodating changes of volume. As before, components corresponding to elements of vessel 100 are identically numbered. The harvesting outlet port 108 is shown in some detail, and includes an exit tube 141 adapted to connection with a applicator or transfer device, a membrane 142 sealing the exit port during processing, and a breakaway cover 143 which maintains the exit tube sterile prior to use. Bag 140 is formed with RF welded seams 145 of sufficient strength and has apertures 146 at the top for hanging in a centrifuge bucket. At the top of bag 140 is shown a third port 148 which communicates with an inner bag 150 having matrix packing material 152 therein. Elements 148, 150, 152 are optional elements and are intended to serve the same function as described above for the platelet enrichment processing vessel 120 of FIG. 8. It will be understood that vessel 140 is adapted for insertion into a centrifuge bucket having a substantially rigid liner forming a recess having the shape of vessel 100 or 120, and that vessel 140 is of a size tailored to assume that shape during centrifuging. The vessels 100, 120, 140 are preferably fabricated and sterilized together with one or more blood bags so as to form an integral phlebotomy set for drawing blood, and storing and processing the cryoprecipitate in an entirely closed and sterile environment. To this end, one or more auxiliary bags are preferably attached to one or more of the ports 110, 112, 148 for the initial drawing of blood and separation of plasma therefrom for provision to the vessel, and for drawing off the cryoprecipitate-depleted plasma from the vessel following the above described processing.

Each of the above described embodiments thus preferably either includes a closed sterile phlebotomy set, or is adapted for docking with the plasma bag of a sterile set. Unlike conventional methods and devices for the isolation of cryoprecipitate, the invention provides for the sterile isolation of cryoprecipitate in a form which may be stored. It also provides a vessel which may be used directly as an applicator in a surgical setting.

The invention being thus described, various modifications will occur to those skilled in the art and all such variations are intended to be included in the scope of the invention as defined by the following claims.

What is claimed is:

1. A vessel for the centrifugal separation and handling of cryogloblin, such vessel comprising
    a hollow body portion having first and second ends,
    a sump extending from and closing said second end,
    a tapered portion of said hollow body extending to and connecting with said sump so as to funnel dense blood products thereto when centrifuged, and
    means defining a port entering the vessel at said tapered body portion for decanting plasma after centrifuging without remixing denser separated products in said sump.

2. A vessel according to claim 1, wherein said sump has an interior volume in the range of two to five percent of the volume of said hollow body portion.

3. A vessel according to claim 1, wherein said first end further includes a hydrophobic micro-porous filter for venting the vessel during transfer of plasma through the port.

4. A vessel according to claim 1, wherein the body portion is non-rigid and wherein the sump further includes a tapered closed tip portion, which may be sliced off to permit extrusion of plasma from the nipple by squeezing of the body portion.

5. A vessel according to claim 1, further comprising a conduit interconnecting said vessel in closed sterile fluid communication with a phlebotomy set having a plasma bag.

6. A vessel for the centrifugal separation and handling of cryoglobin, such vessel comprising
    a hollow body portion having first and second ends,
    a sump extending from and closing said second end,
    a tapered portion of said hollow body extending to and connecting with said sump so as to funnel dense blood products thereto when centrifuged,
    means defining a port entering the vessel at said tapered body portion for decanting plasma after centrifuging without remixing denser separated products in said sump,
    a filter container mounted in the interior of said vessel and having an interior communicating with the interior of said vessel through a filter,
    means defining a port in fluid communication with said filter container for providing fluid material thereto, and
    said filter container communicating with the interior of said vessel such that fluid in said filter container passes by centrifugal pressure through said filter to said interior of said vessel when centrifuged.

7. An improved method of isolating cryoprecipitate by freezing and thawing plasma and subsequently centrifuging the thawed plasma to separate precipitated material therefrom, wherein said isolating is performed on plasma in a separation vessel, and the improvement comprises the steps of
    providing in said separation vessel an interior filter chamber communicating through a filter with the interior of said separation vessel,
    placing cellular material in said interior filter chamber, and
    freezing, thawing and centrifuging said separation vessel with said cellular material in said interior filter chamber whereby certain components of said cellular material separate out with said cryoprecipitate while cell membrane material is retained in said filter.

8. A method of treating a surgical joint with cryoprecipitate, such method comprising the steps of
    1. isolating the cryoprecipitate according to the method of claim 7; and
    2. extruding the cryoprecipitate from the separation vessel onto the surgical joint.

* * * * *